United States Patent [19]

Manabe et al.

[11] Patent Number: 4,610,997
[45] Date of Patent: Sep. 9, 1986

[54] FUNGICIDAL N-ACYLIMIDAZOLES

[75] Inventors: Akio Manabe, Ibaraki; Yoshio Hisada, Amagasaki; Kunihiko Furuzawa, Takarazuka, all of Japan

[73] Assignee: Sumitomo Chemical Company, Limited, Osaka, Japan

[21] Appl. No.: 662,640

[22] Filed: Oct. 19, 1984

[30] Foreign Application Priority Data

Oct. 25, 1983 [JP] Japan ................. 58-199809

[51] Int. Cl.$^4$ ................... A01N 43/50; C07D 233/60
[52] U.S. Cl. .................... 514/397; 514/399; 548/336; 548/341
[58] Field of Search ............... 548/341, 336; 514/397, 514/399

[56] References Cited

U.S. PATENT DOCUMENTS 3,801,636 4/1974 Horrom ....................... 548/341

FOREIGN PATENT DOCUMENTS 53-130661 11/1978 Japan ..................... 548/341

OTHER PUBLICATIONS

Staab, H., *Angew. Chem.* 74, 419 (1962).

March, J., *Advanced Organic Chemistry*, McGraw Hill, New York, 1968, pp. 756-757.
Staab, H., et al., *Chem. Ber.*, 95, 1275-1283 (1962).

*Primary Examiner*—Richard A. Schwartz
*Attorney, Agent, or Firm*—Stevens, Davis, Miller & Mosher

[57] ABSTRACT

N-acylimidazole represented by the formula:

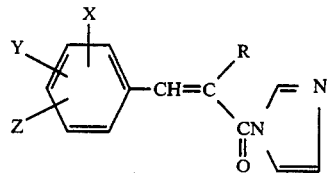

wherein R is a lower alkyl group, and X, Y and Z are, the same or different, each a hydrogen atom, a halogen atom, a lower alkyl group, a halogenated lower alkyl group, a lower alkoxy group, a lower alkylthio group, a cyano group or a nitro group, or two of X, Y and Z, taken together, may form a methylenedioxy group, which is useful for controlling plant diseases.

7 Claims, No Drawings

FUNGICIDAL N-ACYLIMIDAZOLES

The present invention relates to acylimidazoles (hereinafter referred to as "present compound(s)") represented by the formula:

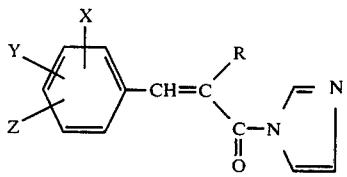

wherein R is a lower alkyl group, and X, Y and Z are, the same or different, each a hydrogen atom, a halogen atom, a lower alkyl group, a halogenated lower alkyl group, a lower alkoxy group, a lower alkylthio group, a cyano group or a nitro group, or two of X, Y and Z, taken together, may form a methylenedioxy group, their production and use as plant disease-controlling agents.

Some kinds of N-acylimidazoles, for example, cinnamoylimidazole and p-chlorobenzoylimidazole, are described in Chem. Ber., 95, 1275 (1962), but there is no description on whether or not these compounds have some physiological activity on plants.

The present inventors made an extensive study on the physiological activity of N-acylimidazoles on plants and as a result, found that the present compounds have a preventive, curative or systemic controlling activity on many plant diseases.

In the present invention, the term "lower" means to have 8 or less carbon atoms. A preferred R is a tertbutyl group or a tert-pentyl group, and preferred X, Y and Z are, the same or different, each a hydrogen atom, a fluorine atom, a chlorine atom or bromine atom, a methyl group, a trifluoromethyl group, a methoxy group, a methylthio group, a cyano group, a nitro group, or two of X, Y and Z, taken together, may form a methylenedioxy group.

Examples of the plant diseases on which the present compounds have a controlling activity are given below:

Blast of rice (*Pyricularia oryzae*), helminthosporium leaf spot of rice (*Cochliobolus miyabeanus*), sheath blight of rice (*Rhizoctonia solani*), powdery mildew of wheat & barley (*Erysiphe graminis* f. sp. hordei, f. sp. tritici), fusarium blight of wheat & barley (*Gibberella zeae*), rust of wheat & barley (*Puccinia striiformis, P. graminis, P. recondita, P. hordei*), snow blight of wheat & barley (*Typhula* sp., *Micronectriella nivalis*), loose smut of wheat & barley (*Ustilago tritici, U. nuda*), eye spot of wheat & barley (*Pseudocercosporella herpotrichoides*), leaf blotch of wheat & barley (*Rhynchosporium secalis*), speckled leaf blotch of wheat & barley (*Septoria tritici*), glume blotch of wheat & barley (*Leptosphaeria nodorum*), melanose of citrus (*Diaporthe citri*), scab of citrus (*Elsinoe fawcetti*), fruit rot of citrus (*Penicillium digitatum, P. italicum*), blossom blight of apple (*Sclerotinia mali*), canker of apple (*Valsa mali*), powdery mildew of apple (*Podosphaera leucotricha*), alternaria leaf spot of apple (*Alternaria mali*), scab of apple (*Venturia inaequalis*), scab of pear (*Venturia nashicola*), black spot of pear (*Alternaria kikuchiana*), rust of pear (*Gymnosporangium haraeanum*), brown rot of peach (*Sclerotinia cinerea*), scab of peach (*Cladosporium carpophilum*), phomopsis rot of peach (Phomopsis sp.), anthracnose of graph (*Elsinoe ampelina*), ripe rot of grape (*Glomerella cingulata*), powdery mildew of grape (*Uncinula necator*), rust of grape (*Phakopsora ampelopsidis*), anthracnose of Japanese persimmon (*Gloeosporium kaki*), leaf spot of Japanese persimmon (*Cercospora kaki, Mycosphaerella nawae*), anthracnose of cucumber (*Colletotrichum lagenarium*), powdery mildew of cucumber (*Sphaerotheca fuliginea*), gummy stem blight of cucumber (*Mycosphaerella melonis*), early blight of tomato (*Alternaria solani*), leaf mold of tomato (*Cladosporium fulvum*), phomopsis blight of eggplant (*Phomopsis vexans*), powdery mildew of eggplant (*Erysiphe cichoracearum*), alternaria leaf spot of brassica (*Alternaria japonica*), white spot of brassica (*Cercosporella brassicae*), rust of Welsh onion (*Puccinia allii*), purple stain of soybean (*Cercospora kikuchii*), anthracnose of soybean (*Elsinoe glycines*), melanose of soybean (*Diaporthe phaseolorum* var. sojae), anthracnose of kidney bean (*Colletotrichum lindemuthianum*), leaf spot of peanut (*Mycosphaerella personatum*), brown leaf spot of peanut (*Cercospora arachidicola*), powdery mildew of pea (*Erysiphe pisi*), early blight of potato (*Alternaria solani*), powdery mildew of strawberry (*Sphaerotheca humuli*), net blister blight of tea (*Exobasidium reticulatum*), white scab of tea (*Elsinoe leucospila*), brown spot of tobacco (*Alternaria logipes*), powdery mildew of tobacco (*Erysiphe cichoracearum*), anthracnose of tobacco (*Colletotrichum tabacum*), cercospora leaf spot of beet (*Cercospora beticola*), scab of rose (*Diplocarpon rosae*), powdery mildew of rose (*Sphaerotheca pannosa*), leaf blight of chrysanthemum (*Septoria chrysanthemiindici*), rust of chrysanthemum (*Puccinia horiana*), gray mold (*Botrytis cinerea*) and stem rot (*Sclerotinia sclerotiorum*) of various crops, and the like.

The present compound, therefore, can be used as an active ingredient for plant disease-controlling agents for use in paddy fields, orchards, tea gardens, pastures, turfs and the like.

The present compound, since it contains a double bond in the molecule, has two geometrical isomers as represented by the formulae,

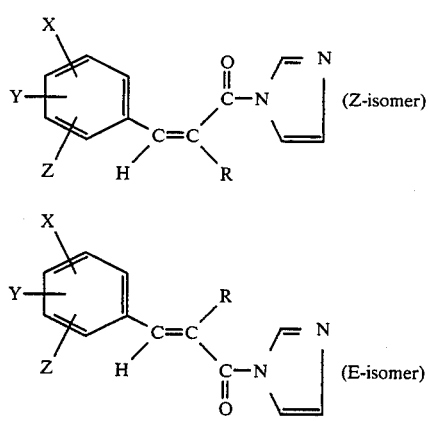

wherein R, X, Y and Z are as defined above, and the both compounds are included in the scope of the present invention.

The present compound can be produced, for example, by the thermal decomposition/decarboxylation of a bisimidazole represented by the formula:

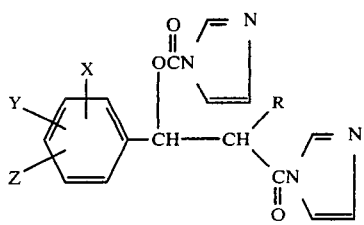 (II)

wherein R, X, Y and Z are as defined above, in the presence or absence of a solvent.

The solvent includes for example aromatic hydrocarbons (e.g. benzene, toluene, xylene), halogenated hydrocarbons (e.g. chlorobenzene, dichlorobenzene), ethers (e.g. dioxane, tetrahydrofuran, diethylene glycol dimethyl ether), nitro compounds (e.g. nitrobenzene), tertiary amines (e.g. pyridine, N,N-diethylaniline, tributylamine, N-methylmorpholine), acid amides (e.g. formamide, N,N-dimethylformamide, acetamide), sulfur compounds (e.g. dimethyl sulfoxide, sulfolane), and mixtures thereof. The reaction is usually carried out at a temperature of 70° to 200° C. for 10 minutes to 2 hours. After completion of the reaction, the present compound can be obtained, for example, by concentrating the reaction mixture, dissolving the residue in an organic solvent, washing the resulting organic solution with water and removing the solvent by evaporation. The present compound thus obtained is purified if necessary by chromatography, distillation, recrystallization and the like.

The product obtained by the method of the present invention is generally a mixture of the foregoing Z- and E-isomers, but the ratio of the both isomers varies with the substituents R, X, Y and Z. When the product is separated and purified, for example, by column chromatography on silica gel, it is not clear which of these geometrical isomers the separated and purified compound corresponds to. But, by measuring the PMR spectrum of these isomers, they are characterized in that one of them is an isomer of which the proton at 2-position of the imidazolyl group is observed in a higher magnetic field (hereinafter referred to as Z-type) and the other is an isomer of which the proton at 2-position of the imidazolyl group is observed in a lower magnetic field (hereinafter referred to as E-type).

The ratio of Z-type to E-type can be calculated by gas chromatography with the integrated value of the proton of the imidazolyl group in PMR spectrum regarded as equivalent to the integrated value of the peak in gas chromatography. That is, in gas chromatography under the condition described later, the retention times of the both are different from each other, that of the Z-type being shorter. Further, it was found that the Z-type can be isomerized into the E-type by irradiation with light.

The bisimidazole compound represented by the foregoing formula (II) is obtained, for example, by reaction a carboxylic acid represented by the formula:

RCH₂COOH (III)

wherein R is as defined above, with n-butyllithium and diisopropylamine, and then reacting the resulting compound with a substituted benzaldehyde represented by the formula:

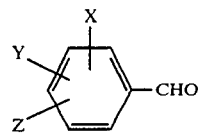 (IV)

wherein X, Y and Z are as defined above, to obtain a hydroxypropionic acid [reference: J. Mulzer, et al., Liebigs Ann. Chem, 1108 (1980)] represented by the formula:

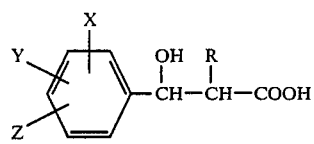 (V)

wherein R, X, Y and Z are as defined above, which is then reacted with 1,1'-carbonyldiimindazole represented by the formula:

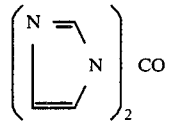 (VI)

Practical and presently preferred embodiments for the production of the present compound as well as that of the starting materials are shown in the following Examples and Reference Examples.

EXAMPLE 1

48.23 Grams (120 mmoles) of N-{2-tert-butyl-3-(4-chlorophenyl)-3-(1-imidazolylcarbonyloxy)-propanoyl}-imidazole, was placed in a round-bottom flask and kept at 190° to 200° C. for 30 minutes with occasional shaking. After cooling, the reaction solution was dissolved in 200 ml of diethyl ether and washed twice with water. The ether layer was concentrated under reduced pressure to obtain 34 g of an oily product. This product was purified by column chromatography on silica gel using a n-hexane/acetone(5/1) mixture as an eluent. The crystal obtained was recrystallized from diisopropyl ether to obtain 14.6 g of N-{α-(tert-butyl)-4-chlorocinnamoyl}imidazole [compound No. 1]. m.p., 95.5°–96.5° C.

| Elementary analysis (for $C_{16}H_{17}N_2OCl$): | | | | |
| --- | --- | --- | --- | --- |
| | C | H | N | Cl |
| Found | 66.84 | 5.99 | 9.71 | 12.38 |
| Calculated | 66.55 | 5.93 | 9.70 | 12.28 |
| PMR | (expressed by δ value with tetramethylsilane as internal standard in deutero chloroform): 7.82 (1H,s) (proton at 2-position of imidazolyl group), 7.32 (1H,m), 7.12 (4H,s), 6.91 (1H,m), 6.81 (1H,s), 1.31 (9H,s) | | | |

EXAMPLE 2

1.0 Gram of the acylimidazole (Z-type) obtained in Example 1 was placed in a Pyrex glass flask and dissolved in 500 ml of acetone. After allowing to stand for 20 hours under irradiation with sunlight, acetone was removed by evaporation under reduced pressure. The residue was recrystallized from diisopropyl ether to obtain 0.24 g of the crystal of E-type acylimidazole [compound No. 3]. m.p., 111.5°–112.5° C.

| Elementary analysis (for $C_{16}H_{17}N_2OCl$): | | | | |
|---|---|---|---|---|
| | C | H | N | Cl |
| Found | 66.43 | 5.83 | 9.66 | 12.35 |
| Calculated | 66.55 | 5.93 | 9.70 | 12.28 |

PMR (expressed by δ value with tetramethylsilane as internal standard in deutero chloroform): 8.24 (1H,s) (proton at 2-position of imidazolyl group), 7.60 (1H,m), 7.50–7.15 (5H,m), 6.80 (1H,s), 1.20 (9H,s).

The Z-type and E-type acylimidazoles obtained in Examples 1 and 2 were gas-chromatographed under the following condition:

| Apparatus | GC-7A (produced by Shimadzu Seisakusho, Ltd.) |
|---|---|
| Column | glass column (length, 750 mm; internal diameter, 3.3 mm) |
| Packing | 5% OV-17, Chromosorb WH |
| Temperature | column, 200° C.; injection chamber, 250° C. |

As a result, it was found that the retention times of the main peaks of the Z-type and E-type were 2.70 minutes and 3.82 minutes, respectively, and that a 2:1 mixed sample of the both exhibited the respective peaks in a 2:1 integration ratio at the same respective retention times as above.

Some examples of the present compounds produced in the same manner as above are shown in Table. 1.

TABLE 1

Acylimidazole compounds represented by the formula,

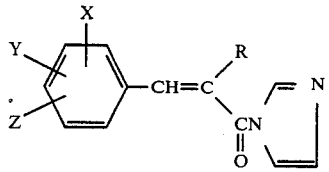

| Compound No. | X, Y, Z | R | Z/E ratio | Physical constant | Retention time on gas chromatography (min) |
|---|---|---|---|---|---|
| 1 | 4-Cl | tert-$C_4H_9$ | 97.6/2.4 | mp 95.5–96.5° C. | 2.70/3.82 |
| 2 | H | " | Z-type | mp 88–89° C. | — |
| 3 | 4-Cl | " | 0.2/99.8 | mp 111.5–112.5° C. | 2.71/3.83 |
| 4 | 2,4-$Cl_2$ | " | Z-type | mp 97–98° C. | — |
| 5 | 2-F | " | Z-type | mp 78.5–79° C. | — |
| 6 | 4-$CH_3$ | " | Z-type | mp 79–80° C. | — |
| 7 | 3-Cl | " | 56/44 | $n_D^{31}$ 1.5628 | 2.62/3.42 |
| 8 | 3,4-$Cl_2$ | " | 62/38 | $n_D^{31}$ 1.5718 | 4.76/6.21 |
| 9 | 4-F | tert-$C_4H_9$ | 73/27 | $n_D^{31}$ 1.5482 | 1.54/2.02 |
| 10 | 3-$OCH_3$ | " | 49/51 | $n_D^{29}$ 1.5556 | 4.04/5.62 |
| 11 | 4-Cl | tert-$C_5H_{11}$ | Z-type | $n_D^{29}$ 1.5680 | — |
| 12 | 4-CN | tert-$C_4H_9$ | Z-type | mp 134–135° C. | — |
| 13 | 4-$SCH_3$ | " | Z-type | mp 96–98° C. | — |
| 14 | 4-$CF_3$ | " | 99.0/1.0 | mp 74–74.5° C. | 1.42/1.88 |
| 15 | 4-$OCH_3$ | " | Z-type | mp 75–76.5° C. | — |
| 16 | 4-Br | " | Z-type | mp 111–111.5° C. | — |
| 17 | 3,4-$OCH_2O$— | " | Z-type | mp 102–104° C. | — |

Reference Example 1

To a mixture of 500 ml of dry tetrahydrofuran and 121.44 g (1.2 moles) of dry diisopropylamine was added dropwise 750 ml (1.2 moles) of a 16% hexane solution of n-BuLi while keeping the temperature at 0° C. or less.

Thereafter, a solution of 62.73 g (0.54 mole) of tert-butylacetic acid in 100 ml of dry tetrahydrofuran was added, and the mixture was stirred at 20° C. for 1 hour. After cooling the reaction solution to −50° C., a solution of 75.9 g (0.54 mole) of p-chlorobenzaldehyde in 100 ml of dry tetrahydrofuran was added dropwise at the same temperature. The cooling bath was then removed to return the temperature of the reaction solution to 20° C., and after allowing to stand for 3 days, the reaction solution was poured into ice water and acidified with hydrochloric acid. After extracting the organic layer with diethyl ether, the extract was concentrated under reduced pressure to obtain 150 g of a solid product. This product was recrystallized from acetonitrile to obtain 83.5 g (60%) of 2-tert-butyl-3-(4-chlorophenyl)-3-hydroxypropionic acid. m.p., 165°–166° C.

| Elementary analysis (for $C_{13}H_{17}O_3Cl$): | | | |
|---|---|---|---|
| | C | H | Cl |
| Found | 60.82 | 6.77 | 13.73 |
| Calculated | 60.82 | 6.67 | 13.81 |

Some examples of the hydroxypropionic acid represented by the formula (V) wherein R is a tert-butyl group produced in the same manner as above are shown in Table 2.

TABLE 2

Hydroxypropionic acid represented by the formula:

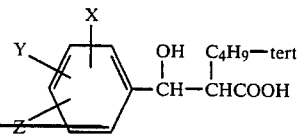

| X, Y, Z | Physical constant |
|---|---|
| 4-Cl | mp 165–166° C. |

TABLE 2-continued

Hydroxypropionic acid represented by the formula:

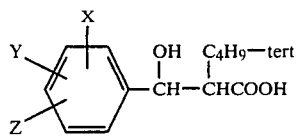

| X, Y, Z | Physical constant |
|---|---|
| H | mp 122–124° C. |
| 2,4-Cl$_2$ | mp 169.5–170.5° C. |
| 2-F | mp 172–172.5° C. |
| 4-CH$_3$ | mp 137–140° C. |
| 3-Cl | mp 132–133° C. |
| 3,4-Cl$_2$ | mp 133° C. |
| 3-OCH$_3$ | mp 105–106° C. |
| 4-CN | mp 185–186° C. |
| 3,4-OCH$_2$O— | mp 121.5–122.5° C. |

Reference Example 3

83.3 Grams (0.324 mole) of 2-tert-butyl-3-(4-chlorophenyl)-3-hydroxypropionic acid and 125 g (0.77 mole) of 1,1'-carbonyldiimidazole were mixed with 700 ml of tetrahydrofuran, and the mixture was heated under reflux for 3 hours with stirring. After concentrating the reaction solution under reduced pressure, water and then diethyl ether were added to the residue which was then washed with water. The ether layer was separated and concentrated to form crystals with a small amount of ether left in the system. The crystal was filtered off and washed with a small amount of ether to obtain 50.6 g (38.5%) of N-{2-tert-butyl-3-(4-chlorophenyl)-3-(1-imidazolylcarbonyloxy)propanoyl}-imidazole. m.p., 69°–71° C.

| Elementary analysis (for C$_{20}$H$_{21}$N$_4$O$_3$Cl): | | | |
|---|---|---|---|
| C | H | N | Cl |
| Calculated 59.93 | 5.28 | 13.98 | 9.84 |
| Found 59.50 | 5.37 | 13.70 | 9.60 |

Some examples of the bisimidazole represented by the formula (II) wherein R is a tert-butyl group, produced in the same manner as above are shown in Table 3.

TABLE 3

Bisimidazole represented by the formula,

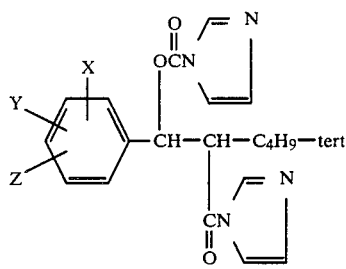

| X, Y, Z | Physical constant |
|---|---|
| 4-Cl | mp 69–71° C. |
| H | mp 114–115° |
| 2,4-Cl$_2$ | mp 125.5–126.5° C. |
| 3-OCH$_3$ | mp 160–162.5° C. |

When the present compounds are used as an active ingredient for plant disease-controlling agents, they may be used as such without adding any other components. Generally, however, they are formulated into Composition-form such as emulsifiable concentrates, wettable powders, suspension formulations, granules, dusts and the like by mixing with an inert carrier such as solid or liquid carriers, surface active agents and other auxiliaries for formulation.

These compositions contain 0.1 to 95.0% by weight, preferably 0.2 to 90.0% by weight of the present compound as an active ingredient.

The solid carrier includes for example fine powders or granules of kaolin clay, attapulgite clay, bentonite, terra alba, pyrophyllite, talc, diatomaceous earth, calcite, corn stalk powder, walnut shell powder, urea, ammonium sulfate, synthetic hydrated silicon dioxide and the like. The liquid carrier includes for example aromatic hydrocarbons (e.g. xylene, methylnaphthalene), alcohols (e.g. isopropanol, ethylene glycol, cellosolve), ketones (e.g. acetone, cyclohexanone, isophorone), vegetable oils (e.g. soybean oil, cotton seed oil), dimethyl sulfoxide, acetonitrile, water and the like.

As the surface active agent used for emulsification, dispersion, wetting and the like, there are given for example anionic surface active agents such as salts of alkyl sulfate, alkyl(aryl)sulfonates, dialkylsulfosuccinates, salts of phosphoric acid esters of polyoxyethylene alkylaryl ether, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation includes for example lignosulfonates, alginates, polyvinyl alcohol, gum arabic, CMC (carboxymethyl cellulose), PAP (isopropyl acid phosphate), etc.

Practical embodiments of the composition according to the invention are illustratively shown in following examples wherein the present compounds are shown by compound number in Table 1, and part means part by weight.

Formulation Example 1

50 Parts of the present compound 1, 3 parts of calcium lignosulfonate, 2 parts of sodium lauryl sulfate and 45 parts of synthetic hydrated silicon dioxide are thoroughly pulverized and mixed to obtain a wettable powder.

Formulation Example 2

10 Parts of the present compound 3, 14 parts of polyoxyethylene styrylphenyl ether, 6 parts of calcium dodecylbenzenesulfonate and 70 parts of xylene are thoroughly mixed to obtain an emulsifiable concentrate.

Formulation Example 3

2 Parts of the present compound 12, 1 part of synthetic hydrated silicon dioxide, 2 parts of calcium lignosulfonate, 30 parts of bentonite and 65 parts of kaolin clay are thoroughly pulverized and mixed, well kneaded with water, granulated and dried to obtain a granule.

Formulation Example 4

25 Parts of the present compound 1, 3 parts of polyoxyethylene sorbitan monooleate, 3 parts of CMC and 69 parts of water are mixed and wet-pulverized until the particle size of the active ingredient is 5 microns or less. A suspension formulation is thus obtained.

Formulation Example 5

2 Parts of the present compound 3, 88 parts of kaolin clay and 10 parts of talc are thoroughly pulverized and mixed to obtain a dust.

These compositions as such or after diluted with water, are applied to foliage or soil. In application to soil, the compositions are sprayed or scattered onto soil surface (if necessary, they are mixed with the soil after spraying or scattering), or soil is drenched with them. Also, an improvement in the controlling activity can be expected by using together with other plant disease-controlling agents. Further, the compositions may also be used in mixture with other fungicides, acaricides, nematocides, herbicides, plant growth regulating agents, fertilizers, soil improvers and the like.

When the present compounds are used as an active ingredient for plant disease-controlling agents, the dosage rate is generally 2 to 300 g/are. When the emulsifiable concentrate, wettable powder, suspension formulation or the like is applied in dilution with water, the application concentration is generally 0.001 to 1.0%, and the granule, dust or the like is applied as such without dilution.

The present compounds are useful as an active ingredient for plant disease-controlling agents will be shown in the following Test Examples. The present compounds are shown by a compound number in Table 1, and compounds used as a control are shown by compound symbol in Table 4.

TABLE 4

| Compound symbol | Chemical structure | Remark |
| --- | --- | --- |
| A | ⟨phenyl⟩—CH=CH—CON⟨N⟩ | Compounds described in Chem. Ber., 95, 1275 (1962). |
| B | Cl—⟨phenyl⟩—CON⟨N⟩ | |

The controlling activity is indicated by numerical values representing six steps of evaluation obtained as follows: The condition of disease of test plants on examination, i.e. the degrees of colony and infected area on the leaves, stems, etc. are observed with the naked eye, and the results of observation are graded into six steps, 0, 1, 2, 3, 4 and 5, as follows:

| | |
| --- | --- |
| 5 | Colony and infected area are not noticed at all. |
| 4 | About 10% of colony and infected area is observed. |
| 3 | About 30% of colony and infected area is observed. |
| 2 | About 50% of colony and infected area is observed. |
| 1 | About 70% of colony and infected area is observed. |
| 0 | Not less than about 70% of colony and infected area is observed, there being no difference in the condition of disease between use of the present compounds and no use of them. |

Test Example 1

Controlling test on gray mold of cucumber (*Botrytis cinerea*) (preventive effect)

Sandy loam was filled in a plastic pot, and cucumber (var., Sagamihanjiro) was sowed and cultivated in a greenhouse. Thereafter, the test compounds each in the form of wettable powder formulated according to Formulation example 1 was diluted with water a prescribed concentration and foliar-sprayed onto the resulting young seedlings in the cotyledonous stage so that the spray liquid was thoroughly attached to the leaf surface. The seedlings were cultivated in a greenhouse for one day after spraying and inoculated with an agar gel containing *Botrytis cinerea*. After inoculation, the seedlings were cultivated at 20° C. for 4 days in a highly humid condition, and the controlling activity was examined. The result is shown in Table 5.

TABLE 5

| Test compound | Application concentration of active ingredient (ppm) | Controlling activity |
| --- | --- | --- |
| 1 | 500 | 5 |
| 2 | " | 5 |
| 3 | " | 5 |
| 4 | " | 4 |
| 5 | " | 4 |
| 6 | " | 5 |
| 7 | " | 5 |
| 8 | " | 5 |
| 9 | " | 5 |
| 10 | " | 4 |
| 11 | " | 5 |
| 12 | " | 5 |
| 13 | " | 5 |
| 14 | " | 5 |
| 15 | " | 5 |
| 16 | " | 5 |
| 17 | " | 5 |
| A | 500 | 0 |
| B | " | 0 |

Test Example 2

Controlling test on leaf rust of wheat (*Puccinia recondita*) (curative effect)

Sandy loam was filled in a plastic pot, and wheat (var., Norin No. 73) was sowed and cultivated in a greenhouse. The resulting young seedlings in the first true leaf stage were inoculated with the spore of *Puccinia recondita* and after inoculation, cultivated at 23° C. for one day in a highly humid condition. Thereafter, the test compounds each in the form of emulsifiable concentrate formulated according to Formulation example 2 was diluted with water to a prescribed concentration and foliar-sprayed onto the seedlings so that the spray liquid was thoroughly attached to the leaf surface. After spraying, the seedlings were cultivated at 23° C. for 12 days under lighting, and the controlling activity was examined. The result is shown in Table 6.

TABLE 6

| Test compound | Application concentration of active ingredient (ppm) | Controlling activity |
| --- | --- | --- |
| 1 | 500 | 5 |
| 2 | " | 5 |
| 3 | " | 5 |
| 4 | " | 4 |
| 5 | " | 4 |
| 6 | " | 5 |
| 7 | " | 5 |
| 8 | " | 5 |
| 9 | " | 5 |
| 10 | " | 4 |
| 11 | " | 5 |
| 12 | " | 5 |
| 13 | " | 5 |
| 14 | " | 5 |
| 15 | " | 5 |
| 16 | " | 5 |
| 17 | " | 5 |
| A | 500 | 0 |

TABLE 6-continued

| Test compound | Application concentration of active ingredient (ppm) | Controlling activity |
| --- | --- | --- |
| B | " | 0 |

Test Example 3

Controlling test on powdery mildew of wheat (*Erysiphe gramini* f.sp. *tritici*) (preventive effect)

Sandy loam was filled in a plastic pot, and wheat (var., Norin No. 73) was sowed and cultivated in a greenhouse. Thereafter, the test compounds each in the form of suspension formulation formulated according to Formulation example 4 was diluted with water to a prescribed concentration and foliar-sprayed onto the resulting young seedlings in the first true leaf stage so that the spray liquid was thoroughly attached to the leaf surface. After spraying, the seedlings were cultivated for one day in a greenhouse and inoculated with the spore of *Erysiphe gramini* f.sp. *tritici*). After inoculation, the seedlings were cultivated for 10 days in a greenhouse, and the controlling activity was examined. The result is shown in Table 7.

TABLE 7

| Test compound | Application concentration of active ingredient (ppm) | Controlling activity |
| --- | --- | --- |
| 1 | 500 | 5 |
| 2 | " | 5 |
| 3 | " | 5 |
| 4 | " | 5 |
| 5 | " | 5 |
| 6 | " | 5 |
| 7 | " | 5 |
| 8 | " | 5 |
| 9 | " | 5 |
| 10 | " | 5 |
| 11 | " | 5 |
| 12 | " | 5 |
| 13 | " | 5 |
| 14 | " | 5 |
| 15 | " | 5 |
| 16 | " | 5 |
| 17 | " | 5 |
| A | 500 | 0 |
| B | " | 0 |

What is claimed is:

1. An acylimidazole represented by the formula:

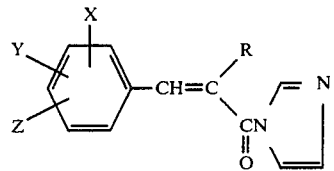

wherein R is a lower alkyl group, and X, Y and Z are, the same or different, each a hydrogen atom, a halogen atom, a lower alkyl group, a halogenated lower alkyl group, a lower alkoxy group, a lower alkylthio group, a cyano group or a nitro group, or two of X, Y and Z, taken together, may form a methylenedioxy group.

2. The compound according to claim 1, wherein R is a tert-butyl group or a tert-pentyl group, X, Y and Z are, the same or different, each a hydrogen atom, a fluorine atom, a chlorine atom or a bromine atom, a methyl group, a trifluoromethyl group, a methoxy group, a methylthio group, a cyano group or a nitro group, or two of X, Y and Z, taken together, may form a methylenedioxy group.

3. N-{α-(tert-butyl)-4-chlorocinnamoyl}imidazole.

4. N-{α-(tert-butyl)-4-cyanocinnamoyl}imidazole.

5. A composition for controlling the diseases of plants caused by fungi which comprises as an active ingredient a fungicidally effective amount of the compound according to claim 1 and an inert carrier.

6. A method for controlling diseases of plants caused by fungi, which comprises applying a fungicidally effective amount of the compound according to claim 1 to the plants.

7. A bisimidazole compound represented by the formula,

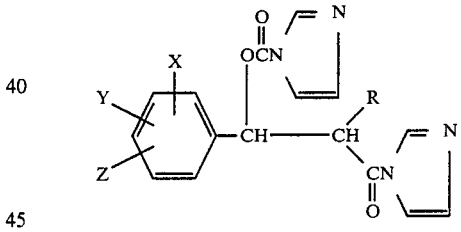

wherein R is a lower alkyl group, and X, Y and Z are, the same or different, each a hydrogen atom, a halogen atom, a lower alkyl group, a halogenated lower alkyl group, a lower alkoxy group, a lower alkylthio group, a cyano group or a nitro group, or two of X, Y and Z, taken together, may form a methylenedioxy group.

* * * * *